(12) United States Patent
Farmer

(10) Patent No.: US 11,097,404 B2
(45) Date of Patent: Aug. 24, 2021

(54) TOOL TORQUE LIMITER

(71) Applicant: Zimmer Biomet Spine, Inc., Westminster, CO (US)

(72) Inventor: Samuel James Farmer, Lafayette, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 498 days.

(21) Appl. No.: 15/809,661

(22) Filed: Nov. 10, 2017

(65) Prior Publication Data

US 2018/0133871 A1     May 17, 2018

Related U.S. Application Data

(60) Provisional application No. 62/420,899, filed on Nov. 11, 2016.

(51) Int. Cl.
    *B25B 23/14*           (2006.01)
    *B25B 23/142*         (2006.01)
    (Continued)

(52) U.S. Cl.
    CPC ........ *B25B 23/141* (2013.01); *B25B 23/1427* (2013.01); *A61B 17/7082* (2013.01);
    (Continued)

(58) Field of Classification Search
    CPC .............. B25B 23/141; B25B 23/1427; B25B 23/1425; B25B 13/461; B25B 13/463;
    (Continued)

(56) References Cited

U.S. PATENT DOCUMENTS 1,415,389 A * 5/1922 Puhl ........................ B25B 15/04
                                                                 81/29
2,618,186 A * 11/1952 Mayer .................. H02K 49/043
                                                                81/473

(Continued)

FOREIGN PATENT DOCUMENTS

DE          3710769 C1     9/1988
DE         20314486 U1    10/2004
(Continued)

OTHER PUBLICATIONS

"International Application Serial No. PCT/US2017/061143, International Search Report dated Jan. 31, 2018", 4 pgs.
(Continued)

*Primary Examiner* — Orlando E Aviles
*Assistant Examiner* — Joel D Crandall
(74) *Attorney, Agent, or Firm* — Schwegman Lundberg & Woessner, P.A.

(57) ABSTRACT

A torque limiter can include a housing and a shaft. The housing can include a housing magnet enclosed within the housing. The shaft can be at least partially surrounded by the housing and can be rotatable within the housing. The shaft can include a shaft magnet integrated with the shaft to magnetically couple with the housing magnet to transmit a torque between the housing and the shaft and configured to uncouple from the housing magnet allowing the shaft to rotate within the housing when a threshold torque is reached.

19 Claims, 12 Drawing Sheets

(51) Int. Cl.
*A61B 90/00* (2016.01)
*A61B 17/70* (2006.01)
*A61B 17/00* (2006.01)

(52) U.S. Cl.
CPC ............... *A61B 2017/00477* (2013.01); *A61B 2017/00876* (2013.01); *A61B 2090/031* (2016.02)

(58) Field of Classification Search
CPC ............ B25B 13/481; A61B 2090/031; A61B 17/7082; A61B 2017/00477; A61B 2017/00876
See application file for complete search history.

(56) References Cited

U.S. PATENT DOCUMENTS

| | | | | |
|---|---|---|---|---|
| 2,644,357 | A * | 7/1953 | Farmer | B23P 19/069 81/57.22 |
| 2,842,240 | A * | 7/1958 | Rice | F16D 43/2024 192/56.32 |
| 5,613,585 | A * | 3/1997 | Tiede | B25B 13/463 192/43.1 |
| 6,142,277 | A * | 11/2000 | Barnett | B25B 13/462 192/43.1 |
| 6,241,616 | B1 * | 6/2001 | Lightcap | F16C 3/03 403/359.5 |
| 2007/0261868 | A1 * | 11/2007 | Gross | A61B 17/8875 173/2 |
| 2009/0218753 | A1 * | 9/2009 | Kramer | H02K 49/108 271/109 |
| 2010/0170763 | A1 | 7/2010 | Lai et al. | |
| 2010/0229693 | A1 * | 9/2010 | Chen | B25B 15/04 81/60 |
| 2016/0288302 | A1 * | 10/2016 | Snook | B25B 15/04 |

FOREIGN PATENT DOCUMENTS

| | | |
|---|---|---|
| EP | 1854587 A2 | 11/2007 |
| EP | 3056314 A1 | 8/2016 |
| WO | WO-2013088158 A2 | 6/2013 |
| WO | WO-2015146734 A1 | 10/2015 |
| WO | 2018089822 | 5/2018 |

OTHER PUBLICATIONS

"International Application Serial No. PCT/US2017/061143, Written Opinion dated Jan. 31, 2018", 5 pgs.

"European Application Serial No. 17805060.5, Response to Communication pursuant to Rules 161(1) and 162 EPC filed Jan. 6, 2020.", 18 pages.

* cited by examiner

TOOL TORQUE LIMITER

CLAIM OF PRIORITY

This application claims the benefit of priority to U.S. Provisional Application Ser. No. 62/420,899, filed on Nov. 11, 2016, which is incorporated herein by reference in its entirety.

BACKGROUND

Torque limiters can be used to limit an amount of torque transferred between two objects, such as two shafts. Torque limiters are often used with tools, such as hand tools and power tools, to limit an amount of torque transferred to a workpiece, such as a screw or bolt. Some torque limiters rely on mechanical means to limit a transferred torque, making them susceptible to wear. Torque limiters can be found in surgical tools and systems to limit the amount of torque applied to a work piece installed in or utilized on a patient.

OVERVIEW

In one example, a torque limiter for limiting a torque transferred from a tool can include a housing and a shaft. The housing can be couplable at a proximal end to a tool, and the housing can include a housing magnet enclosed within the housing. The shaft can be couplable at a distal end to a workpiece and can be enclosed by the housing. The shaft can include a shaft magnet enclosed within the shaft and can be configured to magnetically couple with the housing magnet to transmit a torque between the housing and the shaft and can be configured to uncouple from the housing magnet causing the shaft to rotate within the housing when a threshold torque is reached.

The following, non-limiting examples, detail certain aspects of the present subject matter to solve the challenges and provide the benefits discussed herein, among others.

Example 1 is a torque limiter for limiting a torque transferred from a tool: a housing couplable at a proximal end to a tool, the housing comprising: a housing magnet enclosed within the housing; and a shaft couplable at a distal end to a workpiece and enclosed by the housing, the shaft comprising: a shaft magnet enclosed within the shaft and configured to magnetically couple with the housing magnet to transmit a torque between the housing and the shaft and configured to uncouple from the housing magnet causing the shaft to rotate within the housing when a threshold torque is reached.

In Example 2, the subject matter of Example 1 optionally includes wherein the housing further comprises: a plurality of housing magnets disposed around a central bore of the housing.

In Example 3, the subject matter of Example 2 optionally includes wherein the shaft further comprises: a plurality of shaft magnets disposed within the shaft to align with the plurality of housing magnets.

In Example 4, the subject matter of Example 3 optionally includes wherein each of the plurality of shaft magnets is configured to magnetically couple one of the plurality of housing magnets to transmit a torque between the housing and the shaft, and wherein the plurality of shaft magnets are each configured to uncouple from the one of the plurality of housing magnets, causing the shaft to rotate within the housing when a threshold torque is reached.

In Example 5, the subject matter of Example 4 optionally includes wherein upon rotating the shaft when a threshold torque is reached, each of the plurality of shaft magnets is configured to couple to a different one of the plurality of housing magnets to transmit torque between the housing and the shaft.

Example 6 is a torque limiting driver for driving a workpiece, the torque limiting driver comprising: a housing comprising: a housing bore comprising a central axis; and a housing magnet located proximate the housing bore; a shaft disposed within the housing bore, the shaft comprising: a shaft magnet facing the housing and positioned to generate a magnetic coupling to the housing magnet to enable transmission of a torque between the housing and the shaft, wherein the magnetic coupling is configured to uncouple from the housing magnet allowing the shaft to rotate about the central axis within the housing when a threshold torque is reached; and a clutch connected to the shaft and configured to transfer the torque from the shaft to a workpiece unidirectionally.

In Example 7, the subject matter of Example 6 optionally includes a handle coupleable to the housing to transfer a torque thereto.

In Example 8, the subject matter of any one or more of Examples 6-7 optionally include a coupler removably coupleable to a distal end of the clutch, the coupler configured to releasably receive a driver therein.

In Example 9, the subject matter of any one or more of Examples 6-8 optionally include a proximal bearing coupled to a proximal portion of the housing and a proximal portion of the shaft to enable rotation of the housing relative to the shaft.

In Example 10, the subject matter of any one or more of Examples 6-9 optionally include a distal bearing coupled to a distal portion of the housing and a distal portion of the shaft to enable rotation of the housing relative to the shaft.

In Example 11, the subject matter of any one or more of Examples 6-10 optionally include wherein the housing further comprises: a plurality of housing magnets disposed around a central bore of the housing.

In Example 12, the subject matter of Example 11 optionally includes wherein the shaft further comprises: a plurality of shaft magnets disposed within the shaft and, the shaft magnets coupleable with the plurality of housing magnets.

In Example 13, the subject matter of any one or more of Examples 6-12 optionally include wherein the clutch includes a ratcheting mechanism.

In Example 14, the subject matter of any one or more of Examples 6-13 optionally include the clutch further comprising: a driving member connected to a distal portion of the shaft, the driving member rotatable with the shaft when the shaft receives a torque from the housing; and a driven member engaging the driving member, the driven member configured to rotate the driven member using the torque when the torque is in a first direction about the central axis and configured to rotate independently of the torque when the torque is in a second direction about the central axis.

In Example 15, the subject matter of Example 14 optionally includes the driver member further comprising a driver releaseably engageable with a workpiece to transfer a torque from the driver to the workpiece.

In Example 16, the subject matter of any one or more of Examples 6-15 optionally include wherein the clutch and the housing are not in contact with each other.

In Example 17, the subject matter of any one or more of Examples 6-16 optionally include the shaft further comprising: a shaft bore extending axially through the shaft.

In Example 18, the subject matter of any one or more of Examples 6-17 optionally include wherein the shaft bore comprises a diameter that varies between a proximal end and a distal end of the shaft.

In Example 19, the subject matter of any one or more of Examples 6-18 optionally include wherein an outer surface of the housing is axially fluted.

In Example 20, the subject matter of any one or more of Examples 6-19 optionally include wherein the housing is configured to substantially shield magnetic fields from extending beyond the torque limiter.

Example 21 is a torque limiter comprising: a housing comprising a housing magnet; and a shaft disposed within the housing, the shaft comprising: a shaft magnet facing the housing and positioned to generate a magnetic coupling to the housing magnet to enable transmission of a torque between the housing and the shaft, wherein the magnetic coupling is configured to uncouple from the housing magnet allowing the shaft to rotate when a threshold torque is reached.

In Example 22, the subject matter of Example 21 optionally includes a clutch connected to the shaft and configured to transfer the torque from the shaft to a workpiece unidirectionally.

In Example 23, the device, assembly, or method of any one of or any combination of Examples 1-22 is optionally configured such that all elements or options recited are available to use or select from.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
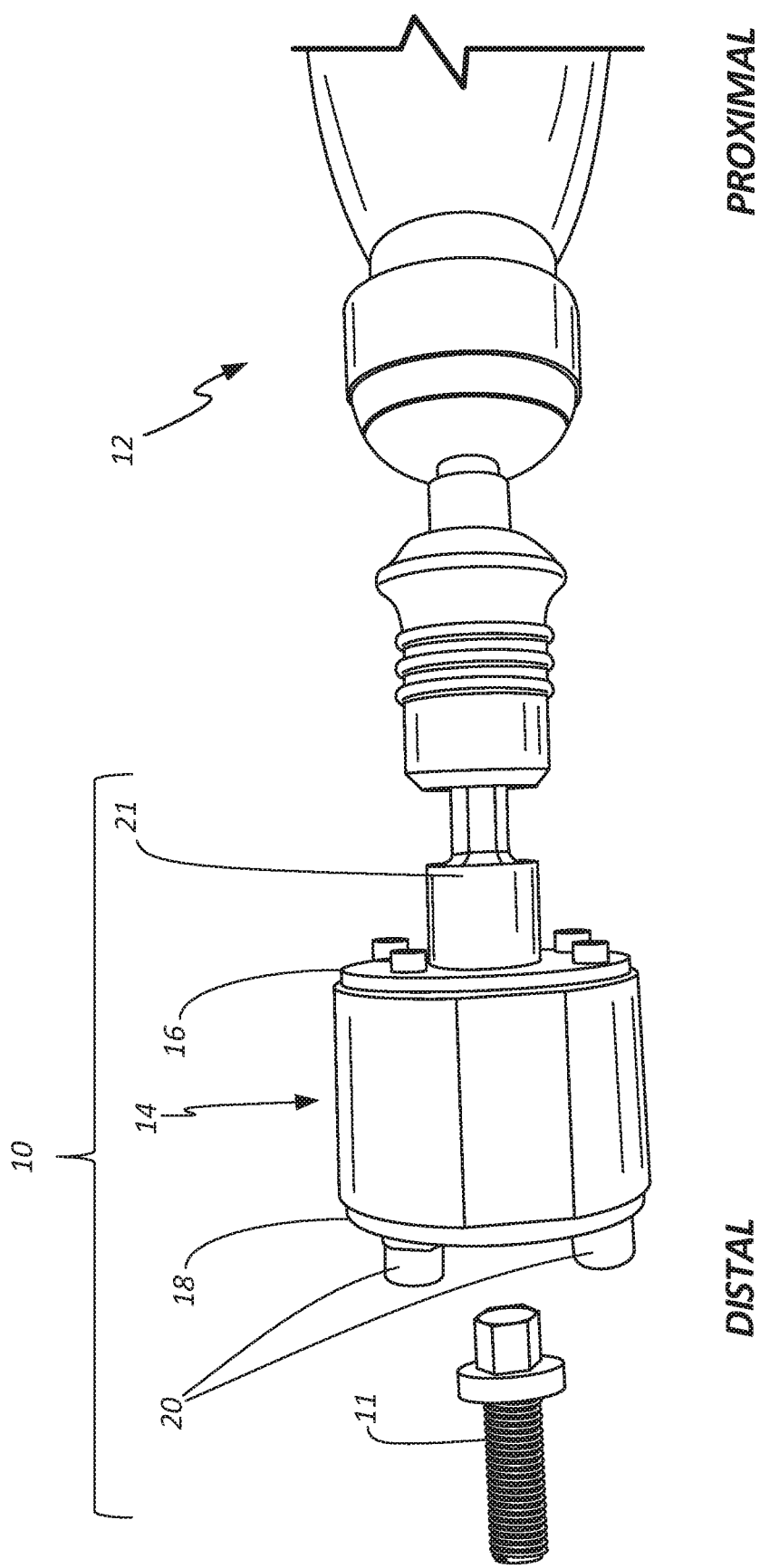
FIG. 1 illustrates a three dimensional view of a tool and torque limiter, in accordance with at least one example of this disclosure.

Torque limiters are commonly paired with drivers for use for driving fasteners, such as screws or bolts, in automotive, construction, and medical industries. In some medical applications, screws or anchors that are over-torqued (or driven too far into a bone or plate) can cause damage to the bone and/or the device being secured thereto (such as a plate). Screws that are under-torqued can become susceptible to backing out (or reversing out) of their bore, compromising the healing process and potentially causing secondary complications. Both under-torqued and over-torqued screws, therefore, can cause a large number of problems during or after a procedure. Within the surgical field, in particular within orthopedics, torque limiting screwdrivers and similar tools are commonplace. For example, orthopedic surgeons performing a spine surgery will often use a torque-limiting device to assist with insertion of pedicle screws to assist in avoiding damage to vertebral bodies.

Torque limiters used in these and similar medical procedures require a low tolerance so that screws, anchors, and related components can be precisely driven into bone (and/or other components, such as plates) without damaging the bone or other components, by driving to a sufficient torque to ensure fastening thereto and prevent reversing or backing out. This problem has been addressed in the past by mechanical and electronic torque limiters. The current state of the art torque-limiting handles utilize purely mechanical components to limit the amount of torque that can transfer down a shaft. These mechanisms can lose their ability to precisely limit torque transfer over time and require recalibration or replacement. The available mechanical torque limiting instruments provide limiting functionality due to the ease with which these tools go out of calibration. Certain mechanical torque-limiting handles can lose their ability to limit predetermined torques almost immediately. Constantly having to re-calibrate torque limiting instruments is time consuming and also results in a lack of confidence in the tool, as the surgeons cannot count on the tool remaining calibrated. Other prior art includes electronic torque indication methods, which can require electrical power for operation. Some of these torque limiters are adjustable so that they can be recalibrated regularly to ensure that they accurately and precisely limit torque. However, these torque limiters can deviate from tolerance very quickly requiring frequent and costly recalibration.

This disclosure addresses a problem with the available mechanical torque limiting instruments involving a lack of accuracy, precision, and requirement for regular calibration. To solve the calibration problem exhibited by known mechanical torque limiting instruments, the inventors looked to use of magnetic fields to provide precise and repeatable torque limiting characteristics in a surgical instrument. This disclosure presents, among other things, a magnetic torque-limiting handle that can use an arrangement of magnets to limit an amount of torque transferred down a shaft. The arrangements of magnets can be referred to as magnetic couplers. In magnetic couplers, torque can be transferred across an air gap by magnetic fields. One example of this disclosure can include two sets of magnets aligned in either a coaxial or face-to-face arrangement. One set of magnets can be attached to a handle, and one set of magnets can be mechanically attached to a shaft. A user can fix the shaft into surgical components and hold and rotate the handle. As the handle rotates, the two sets of magnets diverge from one another. As they diverge, torque is created. When the designed torque limit is exceeded, the magnets snap to their next position. This disclosure presents a design that limits a torque using a magnetic interface, which is less susceptible to wear of torque-limiting components and reduces calibration, repair, and replacement resulting in cost and time savings.

FIG. 1 illustrates a three dimensional view of tool 12 and torque limiter 10, in accordance with at least one example of this disclosure.

Torque limiter 10 can include body 14, proximal cover plate 16, distal cover plate 18, fasteners 20, and plate connector 21. Also shown in FIG. 1 are workpiece 11 and orientation indicators proximal and distal.

Workpiece 11 can be a fastener, as shown in FIG. 1, but can be another tool, coupler, and the like, in other examples. In some examples, workpiece 11 can be configured for use in surgical procedures. In some examples, workpiece 11 can be a machine screw with a hex head, as shown in FIG. 1.

Tool 12 can be a wrench, driver, ratcheting driver, and the like, configured to engage with bits, shafts, and fasteners. Tool 12 can include a handle at a proximal end and a coupler at a distal end configured to engage fasteners, bits, and other tools. In one example, the coupler of tool 12 can be configured with a hex engagement. Connector 21 can be a coupler, such as a shaft, connected to proximal cover plate 16 and configured to couple transfer a torque to body 14. In some examples, connector 21 can include a proximal end having a hex geometry configured to engage common tools, such as the coupler of tool 12.

Proximal cover plate 16 and distal cover plate 18 can be disposed at respective proximal and distal ends of body 14, and can receive fasteners 20 to axially retain the components of body 14. As discussed further below, the distal end of body 14 can be configured to engage workpiece 11 to transfer a torque from tool 12 to workpiece 11.

In operation of one example, a user can apply a torque to tool 12, which can be transferred to body 14 from connector 21. Body 14 can be configured to transfer the torque to workpiece 11 up to a threshold torque. When the threshold torque is reached, body 14 can allow connector 21 to rotate relative to workpiece 11, limiting an amount of torque that can be transferred from tool 12 to work piece 11. In some examples, body 14 can limit the transfer of torque using coupled magnets, such as permanent magnets, as described further below. In other examples, body 14 can limit the transfer of torque using electromagnets, and the like. The level of torque transferred by the handle to the workpiece can be controlled through activation or deactivation of electromagnets within the torque limiter 10. In a torque limiter using permanent magnets, positioning of the magnets can be adjusted or removal/replacement of individual magnets can be utilized to adjust the torque level, among other mechanisms.

Figure 2:
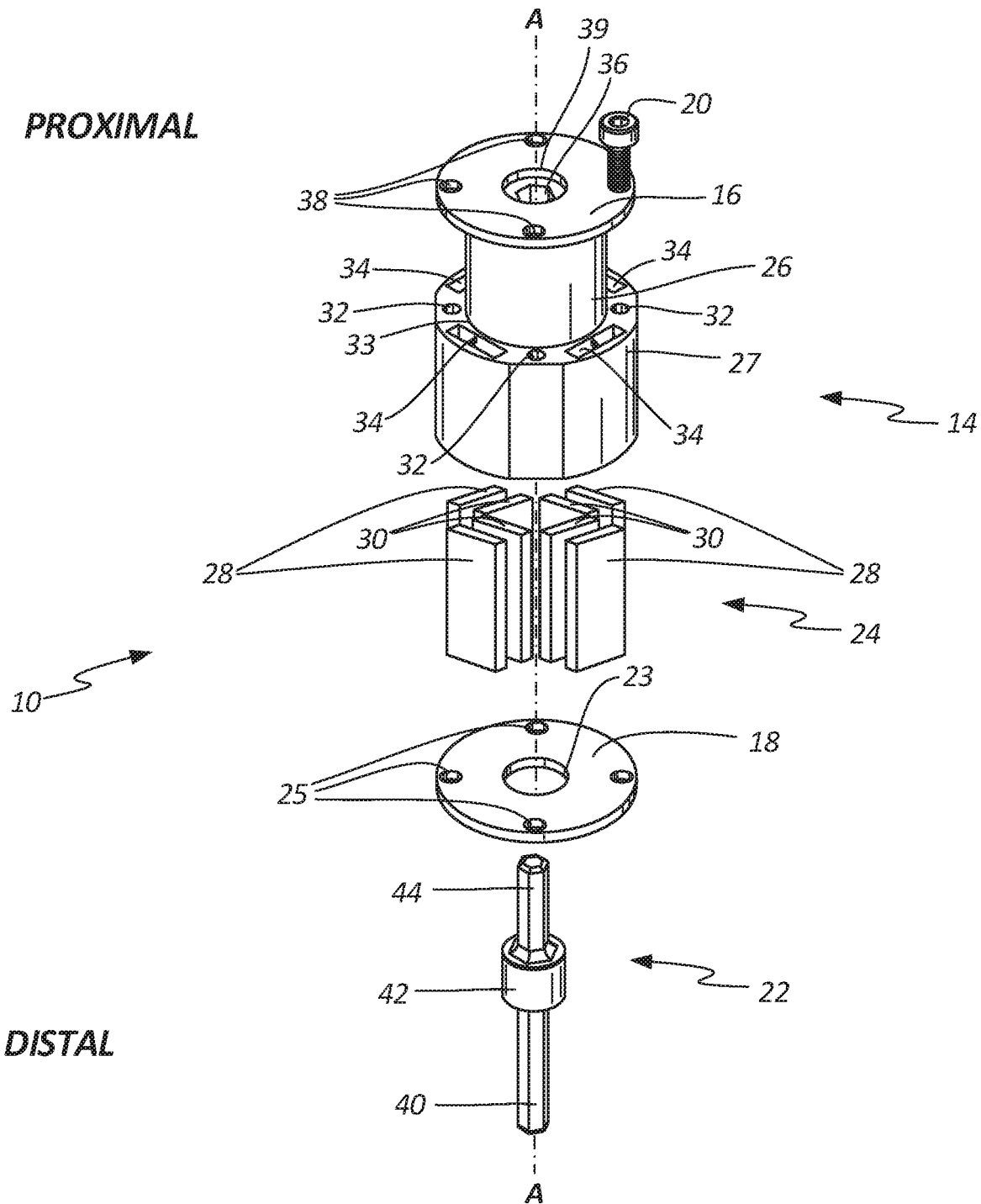
FIG. 2 illustrates an exploded isometric view of a torque limiter, in accordance with at least one example of this disclosure.

FIG. 2 illustrates an exploded isometric view of torque limiter 10, which can include body 14, proximal cover plate 16, distal cover plate 18, fasteners 20, and coupler 22, and coupled magnets 24. Distal cover plate 18 can include central distal bore 23 and distal fastener bores 25. Body 14 can include shaft 26 and housing 27. Coupled magnets 24 can include housing magnets 28 and shaft magnets 30. Housing 27 can include housing fastener bores 32, housing bore 33, and housing magnet slots 34. Shaft 26 can include shaft magnet slots (not shown in FIG. 2), and coupling bore 36. Proximal cover plate 16 can include proximal fastener bores 38 and central proximal bore 39. Coupler 22 can include distal shaft 40, stop 42, and proximal shaft 44. Also shown in FIG. 2 are axis A and orientation indicators proximal and distal. Connector 21 is not shown as attached to proximal cover plate 16, but proximal cover plate 16 can include connector 21 in the examples described in FIG. 2.

Shaft 26, housing 27, proximal cover plate 16, distal cover plate 18, connector 21 (of FIG. 1), and coupler 22 can be comprised of metal, plastic, and the like. In some examples, shaft 26, housing 27, proximal cover plate 16, distal cover plate 18, and connector 21 can be comprised of a non-ferric metal, such as aluminum, to avoid interfering with coupled magnets 24, and that can transfer substantial torque without deforming. Plastic and other non-metallics can also be used with similar benefits.

Shaft 26 can be of a substantially cylindrical geometric shape, but can be of other shapes in other examples. Housing 27 can be similarly geometrically configured, but can include housing bore 32 that can be a cylindrical bore sized to receive shaft 26 so that housing 27 circumferentially encloses shaft 26, leaving distal and proximal ends of shaft 26 exposed.

Shaft 26 can include magnet slots extending axially through shaft 26 and configured to receive shaft magnets 30, allowing shaft magnets 30 to move axially within the slots, but limiting the movement of shaft magnets 30 in all other directions relative to shaft 26. Similarly, housing 27 can include housing magnet slots 34 extending axially through housing 27 and configured to receive housing magnets 28, allowing shaft magnets 30 to move axially within housing magnet slots 34, but limiting the movement of housing magnets 28 in all other directions relative to housing 27.

In some examples, axial movement of shaft magnets 30 within the slots can be used to adjust the magnetic field between shaft magnets and housing magnets 28, which can adjust a threshold torque transferable therebetween. In other examples, shaft magnets and housing magnets can be held in place securely to prevent axial movement to help reduce calibration issues.

Distal fastener bores 25 of distal cover plate 18 can be alignable with housing fastener bores 32 and proximal fastener bores 38 of proximal cover plate. Distal fastener bores 25, housing fastener bores 32, and proximal fastener bores 38 can be configured to receive fasteners 20, which can secure distal cover plate 18 and proximal cover plate 16 to housing 27, and restricting axial movement of coupled magnets 24 within housing 27 and shaft 26. Once secured to housing 27, distal cover plate 18 and proximal cover plate 16 can restrict axial movement of shaft 26 relative to housing 27, leaving shaft 26 free to rotate within housing bore 33.

Coupling bore 36 can extend axially through shaft 26 and can be configured to receive a coupler, such as coupler 22, a workpiece, such as workpiece 11 of FIG. 1, and other tools, such as those configured to perform surgical procedures. Central distal bore 23 can be diametrically sized to be larger than coupling bore 36 so that a workpiece, tool, and the like, can engage coupling bore 36 without interference from distal cover plate 18. Central distal bore 23 can also be diametrically sized to accept stop 42, of coupler 22, within central distal bore 23, limiting axial movement of coupler 22, such as limiting insertion of proximal shaft 44 into coupling bore 36.

Distal shaft 40 and proximal shaft 44 can extend distally and proximally, respectively, from stop 42, along axis A. Distal shaft 40 and proximal shaft 44 can be configured to engage a workpiece, tool, and the like. In some examples, distal shaft 40 and proximal shaft 44 can be configured to engage coupling bore 36 to transmit a torque from coupling bore 36 to a workpiece, such as work piece 11 of FIG. 1.

In operation of one example, a user can transmit a torque from a tool, such as tool 12 of FIG. 1, to connector 21 (of FIG. 1) and into housing 27. Because housing magnets 28 are restricted from moving relative to housing 27, the torque can be transferred from housing 27 to housing magnets 28. Housing magnets 28 can be magnetically coupled to shaft magnets 30 within shaft 26. When housing magnets 28 begin to rotate due to the received torque, a torque can be magnetically transferred to shaft magnets 30 within shaft 26. Because shaft magnets 30 can be secured to shaft 26, the torque transferred to shaft magnets 30 can also be transferred to shaft 26. The torque can then be transferred from shaft 26 (through coupling bore 36) to a work piece, such as work piece 11.

When a second torque applied to housing 27 is larger than a threshold torque, housing magnets 28 will not be able to magnetically transfer the second torque to shaft magnets 30. A threshold torque can be a torque where the force required to move or rotate shaft magnets 30 and shaft 26 with housing 27 is larger than the magnetic force coupling shaft magnets 30 to housing magnets 28. The second torque can cause shaft 26 to rotate in the direction of the second torque relative to housing 27, preventing the second torque from being transferred to a work piece, limiting an amount of torque that can be transferred through torque limiter 10. When torque is not transferred from shaft 26 because shaft 26 rotates relative to housing 27, each one of shaft magnets 30 can engage another of housing magnets 28 so that a torque that is lower than the threshold torque can again be transferred through torque limiter 10.

In some examples, shaft magnets 30 and housing magnets 28 can be replaceable, so that the threshold torque is adjustable for torque limiter 10. In other examples, housing 27 and housing magnets 28 and/or shaft 26 and shaft magnets 30 can be replaceable to adjust the threshold torque. The replacement housings and shafts may include magnets having a weaker or stronger magnetic field, or can include magnets having different spacing or different quantities. As shown in FIG. 2, there can be 4 of housing magnets 28 and shaft magnets 30. In some examples, there can be 1, 2, 3, 5, 6, 7, 8, 9, 10, and the like, of housing magnets 28 and shaft magnets 30. In some other examples, housing magnets 28 and shaft magnets 30 can have a different quantity. For example, there can be 4 of housing magnets 28 and 8 of shaft magnets 30.

Figure 3:
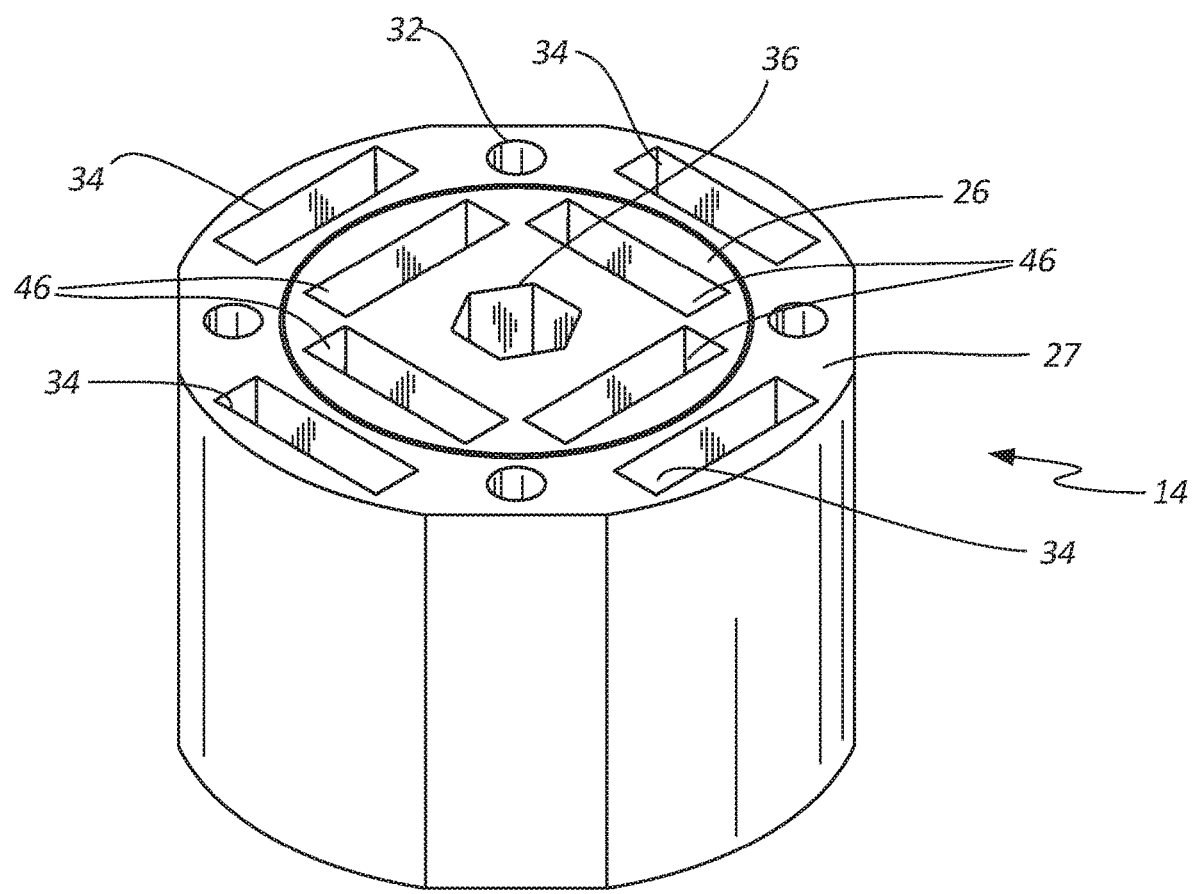
FIG. 3 illustrates an isometric view of a housing and shaft of a torque limiter, in accordance with at least one example of this disclosure.

FIG. 3 illustrates an isometric view of housing 27 and shaft 26. Housing 27 and shaft 26 can be connected and can operate consistently with FIGS. 1 and 2; however, FIG. 3 further shows shaft magnet slots 46. Shaft magnet slots 46 can receive shaft magnets 30, allowing movement of shaft magnets 30 in an axial direction, but limiting the movement of shaft magnets 30 in every other direction relative to shaft 36.

FIG. 3 also shows shaft magnet slots 46 as being of the same quantity as and being radially aligned with housing magnet slots 34. This design can allow for the rotation of shaft 26 relative to housing 27 and quick recoupling of housing magnets 28 to shaft magnets 30.

Figure 4:
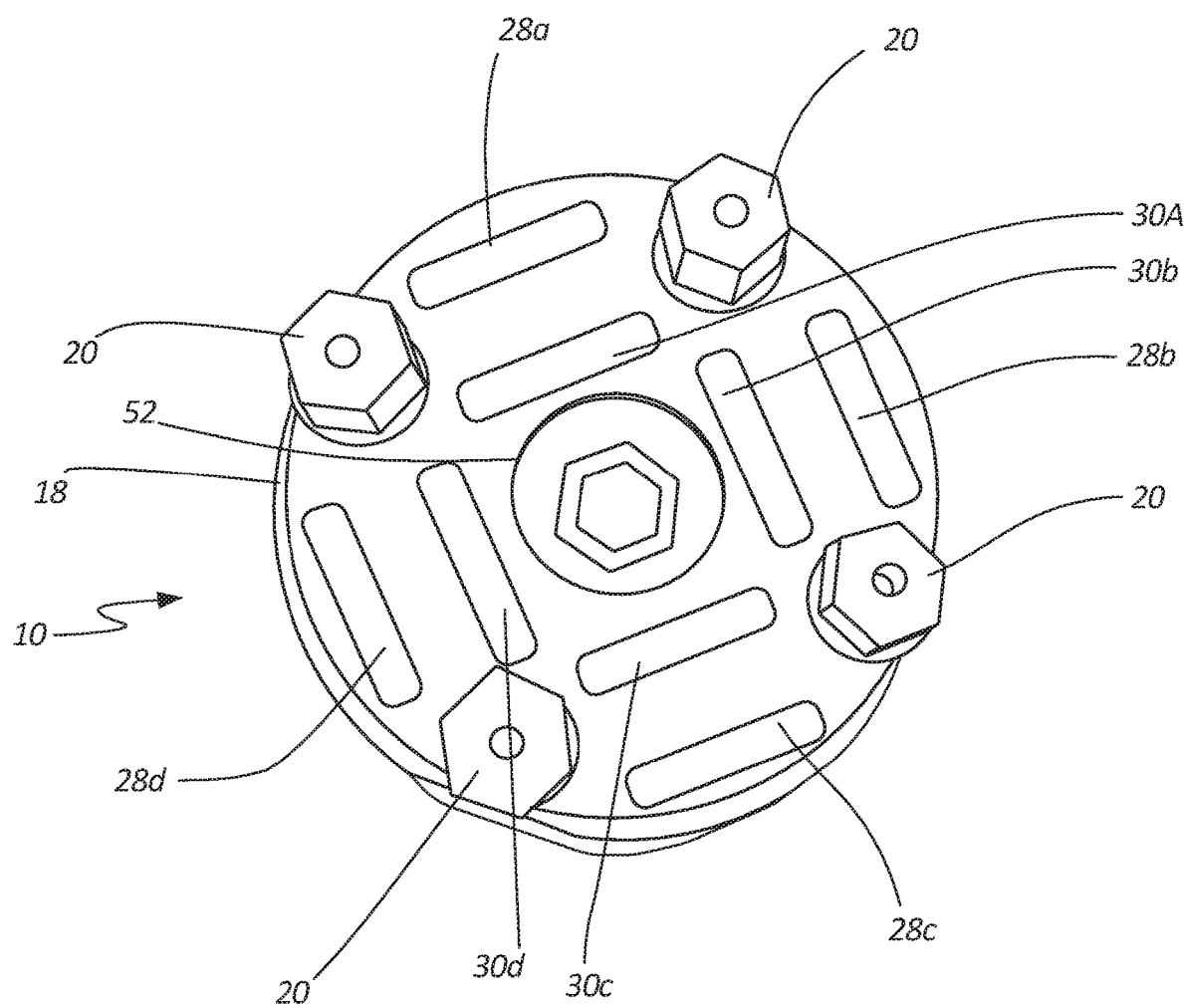
FIG. 4 illustrates a torque limiter from a distal perspective, in accordance with at least one example of this disclosure.

FIG. 4 illustrates torque limiter 10 from a distal perspective, in accordance with at least one example of this disclosure. Torque limiter 10 and its components can be connected and can operate consistently with FIGS. 1-4. However; FIG. 4 additionally shows housing magnets 28a-28d disposed within housing magnet slots 34 and shows shaft magnets 30a-30d disposed in shaft magnet slots 46. FIG. 4 also shows housing magnets 28a-28d and shaft magnets 30a-30d axially secured by distal cover plate 18.

Figure 5:
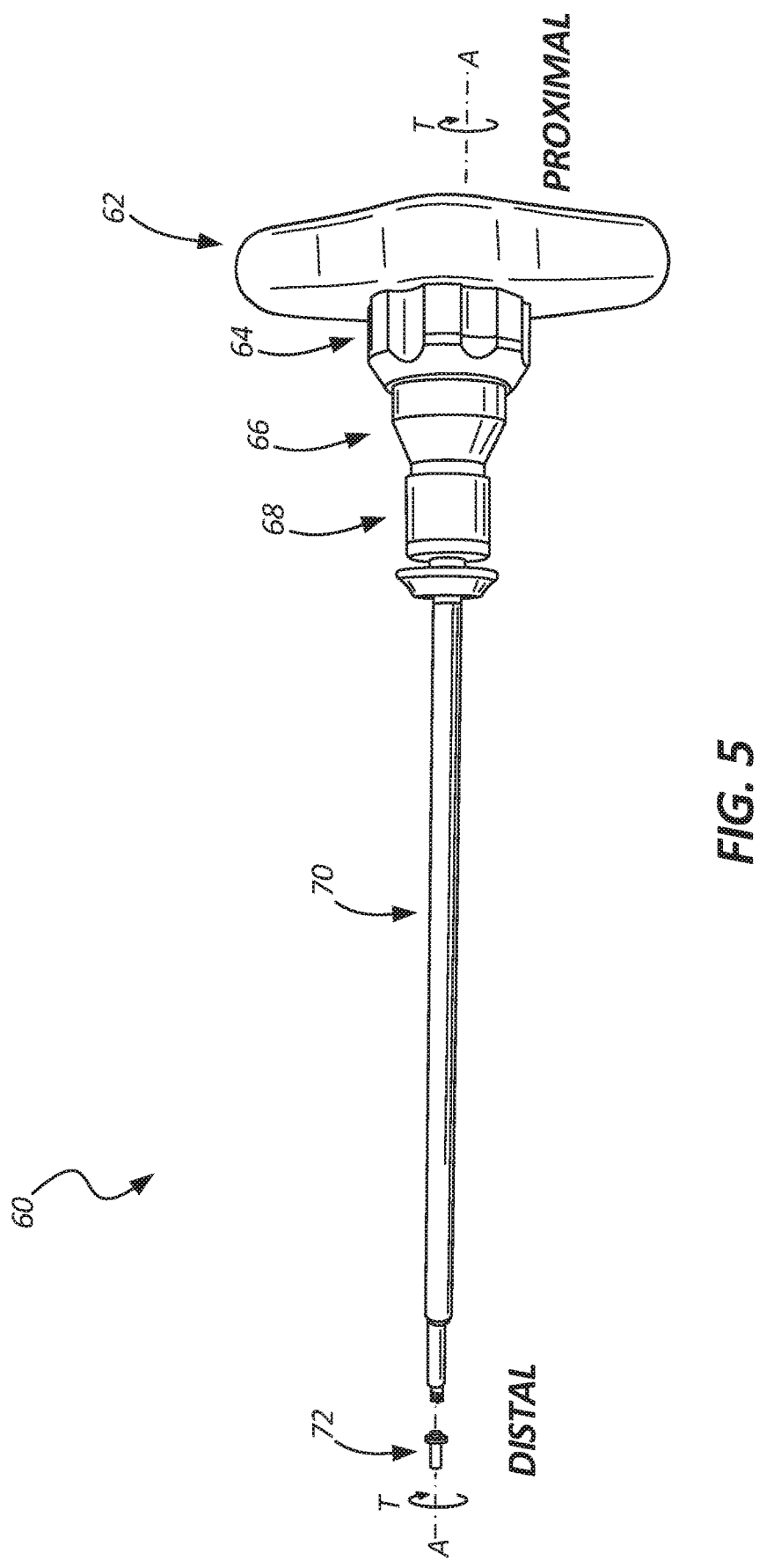
FIG. 5 illustrates a three dimensional view of a torque limiting driver, in accordance with at least one example of this disclosure.
Figure 6:
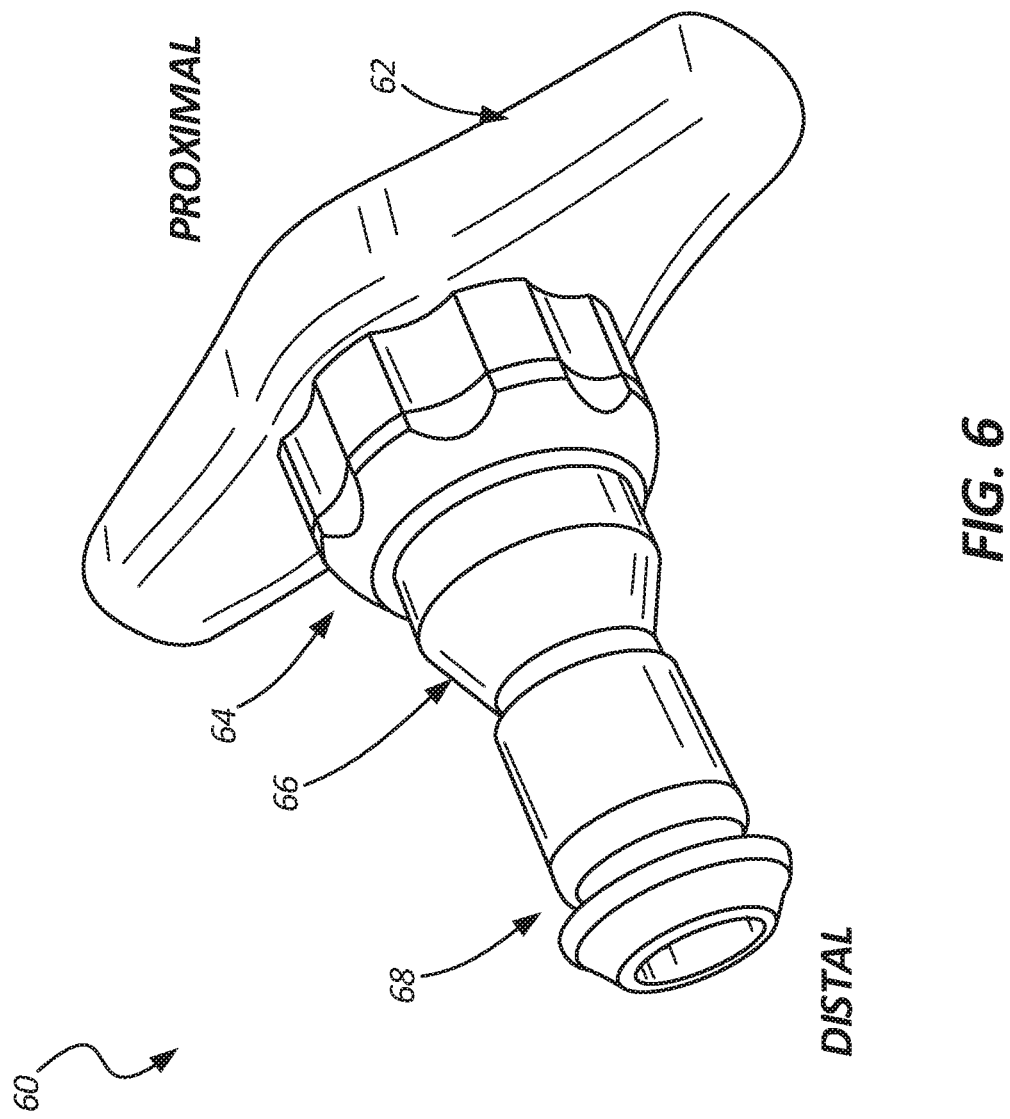
FIG. 6 illustrates a three dimensional view of a torque limiting driver, in accordance with at least one example of this disclosure.

FIG. 5 illustrates a three dimensional view of torque limiting driver assembly 60, in accordance with at least one example of this disclosure. FIG. 6 illustrates another three dimensional view of torque limiting driver assembly without a bit or fastener, in accordance with at least one example of this disclosure. FIGS. 5 and 6 are discussed below concurrently. Torque limiting driver 60 assembly (driver 60) can include handle 62, torque limiter 64, clutch 66, coupler 68, bit (or driver) 70, and fastener 72. FIG. 5 also shows torque T and axis A.

In some examples, torque limiter 64 can be a magnetic torque limiter as described above with respect to FIGS. 1-4 and as described in further detail in FIGS. 7-9 below. Handle 62 can be a rigid member removably coupleable to a housing of torque limiter 64. Handle 62 can be comprised of rigid or substantially rigid materials, such as metals, plastics, composites, combinations thereof, and the like. In other examples, handle 62 can be integrally formed with torque limiter 64. Axis A can be a central longitudinal axis about torque limiter 64, and also about handle 62, clutch 66, coupler 68, and bit 70 in some examples.

Clutch 66 can be a unidirectional clutch, in some examples, configured to transfer torque from torque limiter 64 to coupler 66 and therefore to bit 70 and workpiece 72. In some examples, clutch 66 can be a unidirectional clutch, or a clutch that is configured to transfer rotation in only a single rotational direction about axis A, such as a trapped bearing, sprag clutch, ratcheting clutch, cam clutch, locking roller clutch, locking needle clutch, and the like. In some examples, a proximal end of clutch 66 can be coupled to a distal end of a shaft of torque limiter 64.

Coupler 68 can be a coupler (or quick coupler) configured to releasably receive a bit, such as bit 70. In some examples, coupler 68 can include a barrel and a sleeve axially movable relative to the barrel. In some examples, the sleeve can actuate balls, or other movable members, to move radially relative to the barrel and/or sleeve. A proximal portion of coupler 68 can be removably secured to a distal portion of clutch 66 using an interference interface, in some examples, and a fastened interface in other examples. In some examples, coupler 68 can be sized to receive bit 70 into an internal bore of the barrel and/or sleeve of coupler from a distal end of coupler 68. When inserted into the bore, coupler 68 can lock onto bit 70, preventing relative rotation or axial movement of bit 70 relative to coupler 68 until the sleeve is actuated, axially for example, to release bit 70 from coupler 68.

Bit 70 can be a rigid shaft comprised of material such as plastics, metals, composites, and the like, and configured to transfer a torque from a proximal interface to a distal interface. The proximal interface of bit 70 can be configured to secure to coupler 68 (and to other couplers in other examples) through a geometric profile such as a hexagonal, octagonal, slotted, or grooved interface. The distal interface of bit 70 can include a tooled interface such as standard, cross recessed, hexagonal, hexolobular, square, and the like. The tooled interface can be configured to interface with workpiece 72, which can be a bolt, screw, or other fastener.

In operation of some examples, for example during a procedure where it is desired to secure workpiece 72 to another components (such as a bone, plate, or other substrate), torque T can be applied to handle 62 in a clockwise direction about axis A. Handle 62 can transfer torque T to torque limiter 64, where magnets within torque limiter 64 can transfer torque T, via magnetic coupling, through torque limiter 64 and to clutch 66 when torque T is below a threshold torque. When torque T is above a threshold torque, a shaft of torque limiter 64 can spin relative to a housing of torque limiter 64 to provide a desired torque to workpiece 72 and to help prevent over-torqueing of workpiece 72.

When torque T is below the threshold torque and is transferred to clutch 66, clutch 66 can transfer torque T to coupler 68 and bit 70. However, clutch 66 cannot transfer torque in the opposite rotational direction (counter-clockwise about axis A). When torque T becomes equal to or greater than the threshold torque, the coupled magnets within torque limiter 64 can uncouple and the shaft and housing of torque limiter 64 can rotate relative to each other, preventing the transfer of torque T through torque limiter. When this happens, the internal magnets recouple to different, adjacent magnets, which can cause unwanted counter-clockwise rotation of bit 70 and workpiece 72. Because clutch 66 is unidirectional, clutch 66 can help prevent counter-clockwise rotation of bit 70 during recoupling by allowing torque limiter 64 to rotate counter-clockwise relative the coupler 68 and bit 70, or by free-wheeling. This can help to allow workpiece 72 to be secured to a component at a desired torque. These details of driver 60 are discussed in further detail in the FIGS. below.

Figure 7:
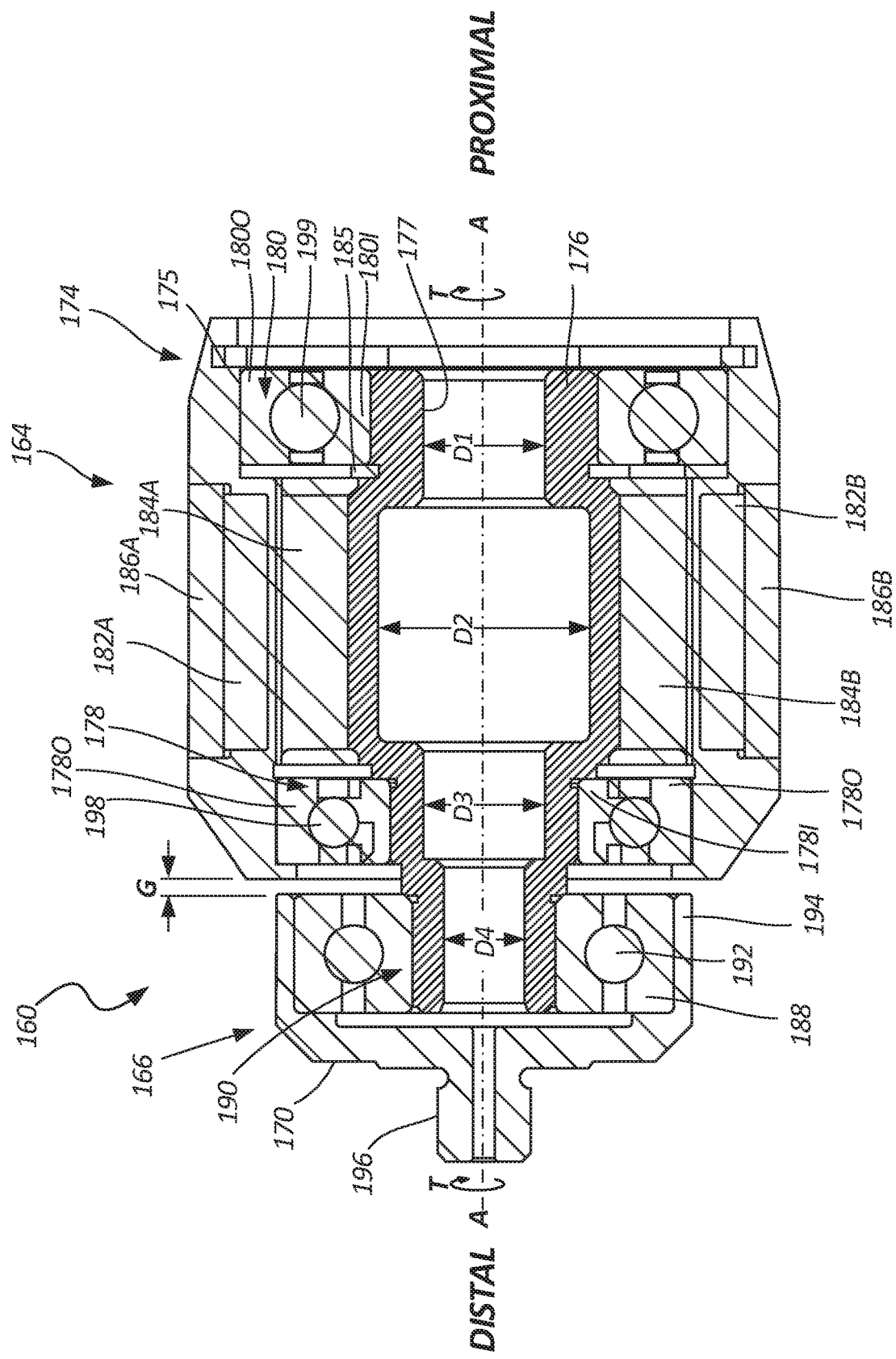
FIG. 7 illustrates a cross-sectional view of a torque limiting driver, in accordance with at least one example of this disclosure.

FIG. 7 illustrates a cross-sectional view of a torque limiting driver 160, in accordance with at least one example of this disclosure. Driver 160 can include torque limiter 164, clutch 166, and tool interface 170. Torque limiter 164 can include housing 174, shaft 176, distal bearing 178, proximal bearing 180, housing magnets 182A and 182B, shaft magnets 184A and 184B, and retaining ring 185. Clutch 166 can include driven portion 188, driving portion 190, and rollers 192. Tool interface 170 can include sleeve 194 and bit 196. Housing 174 can include housing bore 175 and shaft 176 can include shaft bore 177. Distal bearing 178 can include inner race 178I, outer race 178O, and rollers 198. Proximal bearing 180 can include inner race 180I, outer race 180O, and rollers 199. Also shown in FIG. 7 are diameters D1, D2, D3, and D4, axis A, and torque T.

Housing 174 can be a rigid or semi-rigid body comprised of metals, plastics, composites and combinations thereof. Housing bore 175 can be a bore having axis A (which can be a central longitudinal axis) and extending axially entirely through housing 174 in some examples. In other examples, housing 174 can be closed at one or more ends of housing 174. Housing bore 175 can be configured to retain shaft 176 therein. The shape of housing bore 175 can be partially defined by distal and proximal bearings 178 and 180, respectively. Housing magnets 182A and 182B can be located proximate housing bore 175 adjacent shaft magnets 184A and 184B. Housing magnets 182A and 182B can be coupled to housing and in some examples releasably coupled to housing. Housing magnets 182A and 182B can be secured to housing 174 using an interference fit in some examples, and can be fastened, welded, glued, or otherwise affixed to housing 174 in other examples. Shaft magnets 184A and 184B and housing magnets 182A and 182B can be permanent magnets such as metallic magnets, rare-earth magnets, composite magnets, and the like.

In some examples, housing 174 can have a thickness sufficient to substantially shield magnetic fields produced by housing magnets 182 and/or shaft magnets 184 from extending beyond driver 160. In some examples, housing 174 can have a thickness of 0.5 millimeters (mm), 1 mm, 2, mm, 3, mm, 4 mm, and the like. In some of these examples, housing 174 can be comprised entirely or in part of materials that shield magnetic fields from propagation outside housing 174. For example, housing 174 can be comprised of ferromagnetic materials such as iron, nickel, cobalt, and alloys and combinations thereof. In one example, housing 174 can be comprised of mu-metal. In other examples, the thickness of housing 174 can be selected to provide a desired balance of the weight of driver 160 and the magnetic field emitted from driver 160 beyond housing 174.

Housing flutes 186A and 186B can be two (or two of many in some examples) axially extending channels of an outer surface of housing 174. Housing flutes 186 can provided an uneven exterior profile for improved grip and can help to reduce a weight of housing 174.

Shaft 176 can be a rigid or semi-rigid body comprised of metals, plastics, composites and combinations thereof. Shaft 176 can be disposed within housing 174 and within housing bore 175. Shaft 176 can be rotatable within and relative to housing 174, which can be enabled by distal bearing 178 and proximal bearing 180. More specifically, inner race 178I of distal bearing 178 and inner race 180I of proximal bearing 180 can be coupled or secured to shaft 176 and outer race 178O of distal bearing 178 and outer race 180O of proximal bearing 180 can be coupled or secured to housing 174, such that rollers 198 and 199 help enable rotation of shaft 176 relative to housing 180. In some examples retaining ring 186, which can be a cylindrical member having a relatively short height, can help position proximal bearing 180 relative to housing 174 and shaft 176 and can help maintain the positions of these components.

In some examples, shaft 176 can include bore 177 having diameters D1, D2, D3, and D4, where each diameter can be sized based on an outer diameter of shaft 176 at that portion of shaft 176. For example, diameter D1 is sized based on a size of proximal bearing 180, diameter D2 is sized based on a size of shaft magnets 184, diameter D3 is sized based on a size of distal bearing 178, and diameter D4 is sized based on a size of clutch 166. In this way, shaft 176 can be sized and shaped to reduce a weight of driver 160, helping to decrease power required to operate driver 160, helping to decrease fatigue of an operator of during a procedure or operation. In some other examples, shaft 176 can be solid and therefore may not include shaft bore 177.

Driven portion 188, driving portion 190, and rollers 192 of clutch 166 can together form a unidirectional clutch. In the example of FIG. 7, clutch 166 can be a trapped roller clutch, but clutch 166 can be other types of unidirectional clutches in other examples, as discussed above and as shown in FIGS. 8 and 9 below. Driving portion 190 can be coupled (either releasably or fixedly) to a distal portion of shaft 176. In some examples, shaft 176 can be insertable into driving portion 190. Driven portion 188 can be engageable with driving portion 190 via rollers 192. Rollers 192 can be cylindrical rollers in some examples and can be balls or spheres (as shown in FIG. 7) in other examples.

Tool interface 170 can include sleeve 194 and bit 196. Bit 196 can be a tool configured to interface with fastener heads, as discussed above with respect to bit 70 of FIG. 5. However, in the example of FIG. 7, tool interface 170 can be relatively short, axially, and can be integrated with sleeve 194 to secure to clutch 166, such that a coupler is not required. In some examples, driver 160 can include a plurality of bits 170 releasably coupleable to clutch 166, where the plurality can include bits of different tooled interfaces (e.g. cross-slot, standard, hex, etc.).

In operation of some examples, torque T can be applied to housing 174 of torque limiter 164. Because outer races 178O and 180O and housing magnets 182A and 182B are coupled to housing 174, torque T will be transferred to these components. When torque T is less than a threshold torque, housing magnets 182A and 182B can drive shaft magnets 184A and 184B through a magnetic coupling, transferring torque T thereto. Because shaft magnets 184A and 184B are coupled to shaft 176, shaft 176 can be driven by shaft magnets 184A and 184B, transferring torque T therewith. Inner races 178I and 180I along with rollers 198 and 199 will also rotate with shaft 176. As shaft 176 rotates about its central axis A, the distal portion of shaft 176 rotates, rotating driving portion 190 of clutch 166.

When torque T has a clock-wise rotational direction about axis A, driving portion 190 engages rollers 192 and transfers torque T to driven portion 188 to rotate driven portion 188 in a clock-wise rotational direction about axis A. Because tool interface 170 is coupled to driven portion 188, tool interface 170 is also driven to rotate in a clock-wise rotational direction about axis A. Tool interface 170 can receive torque T and transfer torque T to a fastener. However, when the torque transferred to driving portion 190 is in a counter-clockwise rotational direction about axis A, the torque will not transfer to driven portion 188 as driving portion 190 will free-wheel, or rotate relative to driven portion 190. This can allow driver 160 to be used as a ratcheting or unidirectional driver. In some other examples, the driver 160 may not include a clutch 166 and the torque T is transferred in either rotational direction.

Driver 160 can be used to transfer torque T to a workpiece or fastener in a clockwise rotational direction about axis A until a threshold torque is reached. In some examples, the threshold torque can be for example, 0.01 newton meters (Nm), 0.1 Nm, 1 Nm, 10 Nm, 100 Nm, and the like. Once torque T reaches or exceeds the threshold torque in a clock-wise rotational direction, housing magnets 182A and 182B decouple from shaft magnets 184A and 184B allowing housing 174 to spin relative to shaft 176. When this happens, housing 174 rotates in a clock-wise direction (the direction of torque T), and each of housing magnets 182A and 182B can couple to another of shaft magnets. This decoupling prevents a torque T greater than the threshold torque from being transferred to a fastener or workpiece, which can set a desired torque for the workpiece or fastener and can help prevent over-torque or over-tightening of fasteners to bones or plates, for example.

In an example where only two pairs of magnets are used, housing magnet 182A can decouple from shaft magnet 184A allowing housing 174 to rotate relative to shaft 176 and housing magnet 182A can couple to shaft magnet 184B. In this example, housing 174 can turn approximately half a turn (when the magnets are spaced evenly about the circumference of housing 174 and shaft 176 and when housing magnets 182 have the same polarity). In an example where only one pair of magnets is used, housing 174 can rotate about one revolution before the housing magnet (182A) recouples to the same and only shaft magnet (184A). In other examples, there may be more pairs of magnets, such as 3, 4, 5, 6, 7, 8, 9, 10, 20, and the like. In these examples, when housing 174 decouples it can turn by the ratio of one revolution over the number of pairs of magnets. For example, housing 174 would turn one quarter of a rotation when decoupled relative to shaft 176 if driver 160 included 4 pairs of magnets.

In some examples where odd numbers of pairs of magnets are used, such as 3, 5, 7, and 9, all of housing magnets 182 can be of the same magnetic polarity (e.g., north) and all shaft magnets 184 can be of the same magnetic polarity (e.g., south-opposite of housing magnet 182 polarity). This prevents magnets of the same polarity from aligning during recoupling and helps maintain calibration of driver 160.

In other examples, where an even number of pairs of magnets are used, such as 4, 6, or 8 magnets, housing magnets 182 can be arranged in alternating polarity and shaft magnets 184 can be arranged in alternating polarity. This can increase the amount of torque that is transferable between coupled magnets, because adjacent magnets on the opposite race will resist rotation due to opposing forces created by magnets of the same polarity. For example, if there are four housing magnets 182A-D and four shaft magnets 184A-D, each A and C magnet can have a north polarity and each B and D can have a south polarity. In this arrangement, housing magnet 182A can be coupled to shaft magnet 184B, housing magnet 182B can be coupled to shaft magnet 184C, housing magnet 182C can be coupled to shaft magnet 184D, and housing magnet 182D can be coupled to shaft magnet 184A.

Consider, for example, coupling of housing magnet 182B and shaft magnet 184C, where adjacent shaft magnets are 184B and 184D. Because shaft magnets are 184B and 184D are of the same polarity as housing magnet 182B, housing magnet 182B will receive opposing forces from shaft magnets 184B and 184D, resisting uncoupling of housing magnet 182B and shaft magnet 184C (and therefore all of the coupled pairs). This can increase the amount of torque that can be transferred between pairs of magnets.

In some examples, during driving or torqueing a workpiece, tool interface 170 can be engaged with a workpiece, such that when a threshold torque is reached, tool interface 170 can remain engaged with the workpiece. During the process of the magnets decoupling, housing 174 spins in a clock-wise direction relative to shaft 176, and housing and shaft magnets 184 and 182 recouple (or couple to other magnets), shaft 176 (and therefore tool interface 170 and the workpiece coupled thereto) can rotate in a counter-clockwise direction when shaft magnets 184 recouple with housing magnets 182. This effect can be caused by the magnetic force between the pairs while coupling together with torque T being continuously applied to housing 174. That is, housing 174 continues to rotate clock-wise, so shaft 176 rotates counter-clockwise, where housing magnets 182 can recouple to the same shaft magnets 184, in some examples. This action can rotate tool interface 170 and therefore the work piece in a counter-clockwise direction if not controlled, preventing a desired torque of the workpiece from being delivered thereto.

This effect can also be caused by use of an arrangement of alternating polarity of shaft magnets 184 and alternating polarity of housing magnets 182 (discussed above), because each shaft magnet cannot couple to the adjacent housing magnet, but will instead be repelled by it. In this case, each housing magnet must rotate past the adjacent shaft magnet to the next housing magnet of opposite polarity. In operation of this arrangement, torque T applied to housing 174 and resistance from the workpiece can cause recoupling to previously coupled pairs. However, clutch 166 can be used to help prevent this action.

Because clutch 166 is a unidirectional clutch, when shaft 176 rotates in a counter-clockwise direction during the recoupling of pairs of magnets, clutch 166 allows shaft 176 to rotate together with driving portion 190, but rollers 192 do not engage driven portion 188 and driving portion 190 freewheels, or rotates relative to driven portion 188. This forces housing magnets 182 to each couple to different shaft magnets 184 (in the case where two or more pairs are used). This can help prevent the recoupling action from causing tool interface 170 to back the work piece or fastener out, helping to maintain torque T just below the threshold torque or at a desired torque (torque set point). The design of driver 160 can further allow another torque T that is above the threshold torque to be applied (as many times as desired) to the driver to ensure the desired torque of the workpiece has been delivered.

Further, clutch 166 and housing 174 can be separated by gap G, which can be 0.1 millimeter (mm), 1 mm, 10 mm, and the like. This separation can help prevent contact between housing 174 and clutch 166, which can help to ensure that torque is not transferable between housing 174 and clutch 166 except through shaft 176. In some examples, shaft 176 can include an undercut to ensure that clutch 166 cannot move proximally closer to housing 174 and therefore cannot contact housing 174.

Though the examples above are described with respect to a torque in a clock-wise direction. Driver 160 can be configured to selectively transfer and deliver a torque in a counter-clockwise direction.

Figure 8:
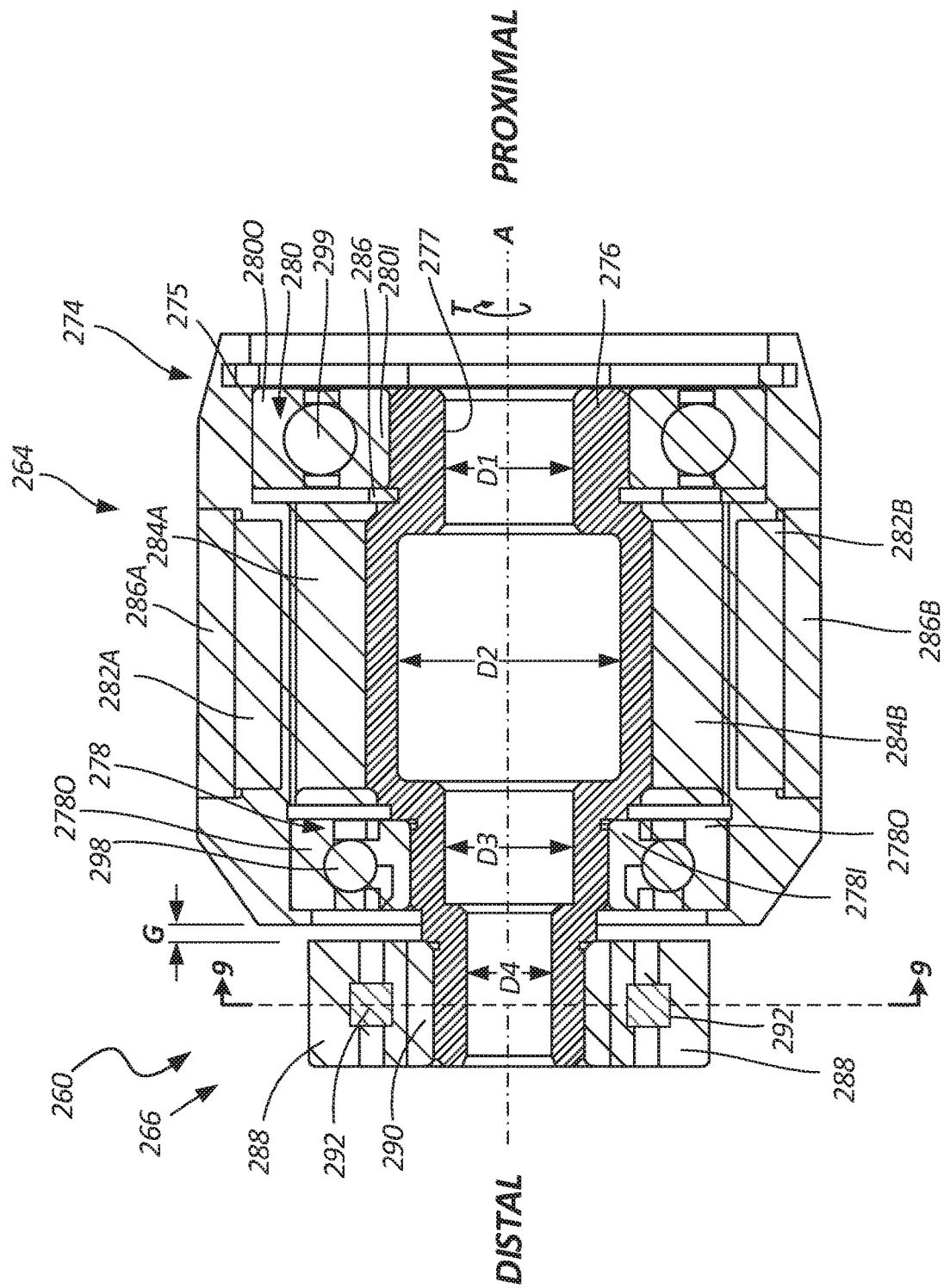
FIG. 8 illustrates a cross-sectional view of another torque limiting driver, in accordance with at least one example of this disclosure.

FIG. 8 illustrates a cross-sectional view of a torque limiting driver 260, in accordance with at least one example of this disclosure.

Driver 260 can include torque limiter 264, clutch 266, and tool interface 270. Torque limiter 264 can include housing 274, shaft 276, distal bearing 278, proximal bearing 280, shaft magnets 282A and 282B, housing magnets 284A and 284B, and retaining ring 286. Housing 274 can include housing bore 275 and shaft 276 can include shaft bore 277. Distal bearing 278 can include inner race 278I, outer race 278O, and rollers 298. Proximal bearing 280 can include inner race 280I, outer race 280O, and rollers 299. Also shown in FIG. 7 are diameters D1, D2, D3, and D4, axis A, and torque T. Driver 260 can be similar to driver 160, except that clutch 266 can include driven portion 288, driving portion 290, and pawls 292.

Driver 260 can operate consistently with driver 160 described in FIG. 7 above; however, in driver 260, a pawl and gear interface can provide unidirectional clutching action. For example, pawls 292 can engage teeth of driving portion 290 (as shown below in FIG. 9 in further detail). In operation, pawls 292 can transfer torque in a clockwise rotational direction about axis A and can allow driving portion 290 to freewheel or rotate relative to driven portion 288 when driving portion 290 rotates in a counter-clockwise rotational direction about axis A.

Though not shown in FIG. 8, clutch 266 can engage a coupler similar to driver 60 of FIGS. 5 and 6 where coupler 68 is securable to an outside diameter of clutch 66.

Figure 9:
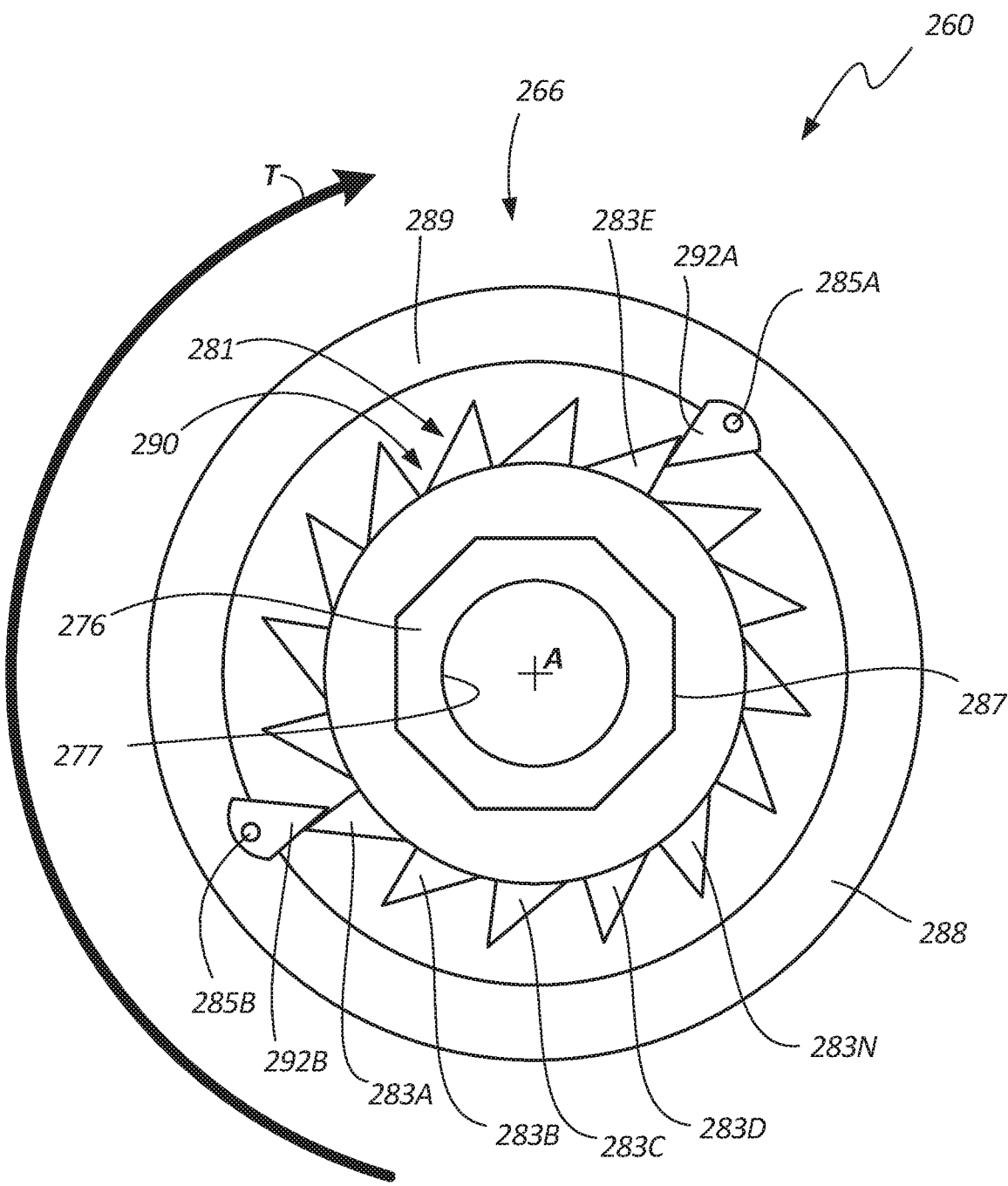
FIG. 9 illustrates a cross-sectional view of a torque limiting driver across section 9-9 of FIG. 8, in accordance with at least one example of this disclosure.

FIG. 9 illustrates a cross-sectional view of torque limiting driver 260 across section 9-9 of FIG. 8, in accordance with at least one example of this disclosure. Driver 260 can include clutch 266 and shaft 276, which can include shaft bore 277. Clutch 266 can include driven portion 288, driving portion 290, and pawls 292A and 292B. Driving portion 290 can include ratchet 281, which can include teeth 283A-283N. Driven portion 288 can include hinges 285A and 285B, ratchet bore 287, and outer race 289.

Shaft 276 can releasably (or fixedly in some examples) couple to driving portion 290 at ratchet bore 287. In some examples, ratchet bore 287 can have an octagonal cylindrical shape complementary with shaft 276 to securably engage with shaft 276 and to prevent relative rotation thereto. Teeth 283A-283N can be integrally formed with an internal race of driving portion 290 and can extend radially from the race forming ratchet 281, which can be a unidirectional gear.

Pawls 292A and 292B can be pivotably or hingeably coupled to outer race 289 through hinges 285A and 285B, respectfully. Pawls 292A and 292B can be hinged such that they hinge or pivot to allow teeth 283A-283N to pass in a counter-clockwise rotational direction about axis A and engage teeth 283A-283N causing clockwise torque (such as torque T) to be transferred from teeth 283A-283N to pawls 292A and 292B and therefore to outer race 289 and allow driving portion 290 to drive driven portion 288 in a clockwise rotational direction about axis A.

Because clutch 266 is a unidirectional ratcheting clutch, when shaft 276 rotates in a counter-clockwise direction during the recoupling of magnetic pairs, as described above with respect to FIG. 7, clutch 266 allows shaft 276 to rotate together with driving portion 290, but pawls 192 do not engage teeth 283A-283N allowing driving portion 290 to freewheel. This can help prevent the magnetic recoupling action from causing a bit to back the work piece or fastener out, helping to maintain torque T at a desired torque.

Though FIG. 9 is described as having a pawl hinged to an outer race of clutch 266, pawls 292 can be on an inner race of clutch 266 in other examples, where the fixed teeth extend radially inward from outer race 288. Similarly, more or fewer than two pawls can be included, such as 1, 3, 4, 5, 6, and the like.

Figure 10:
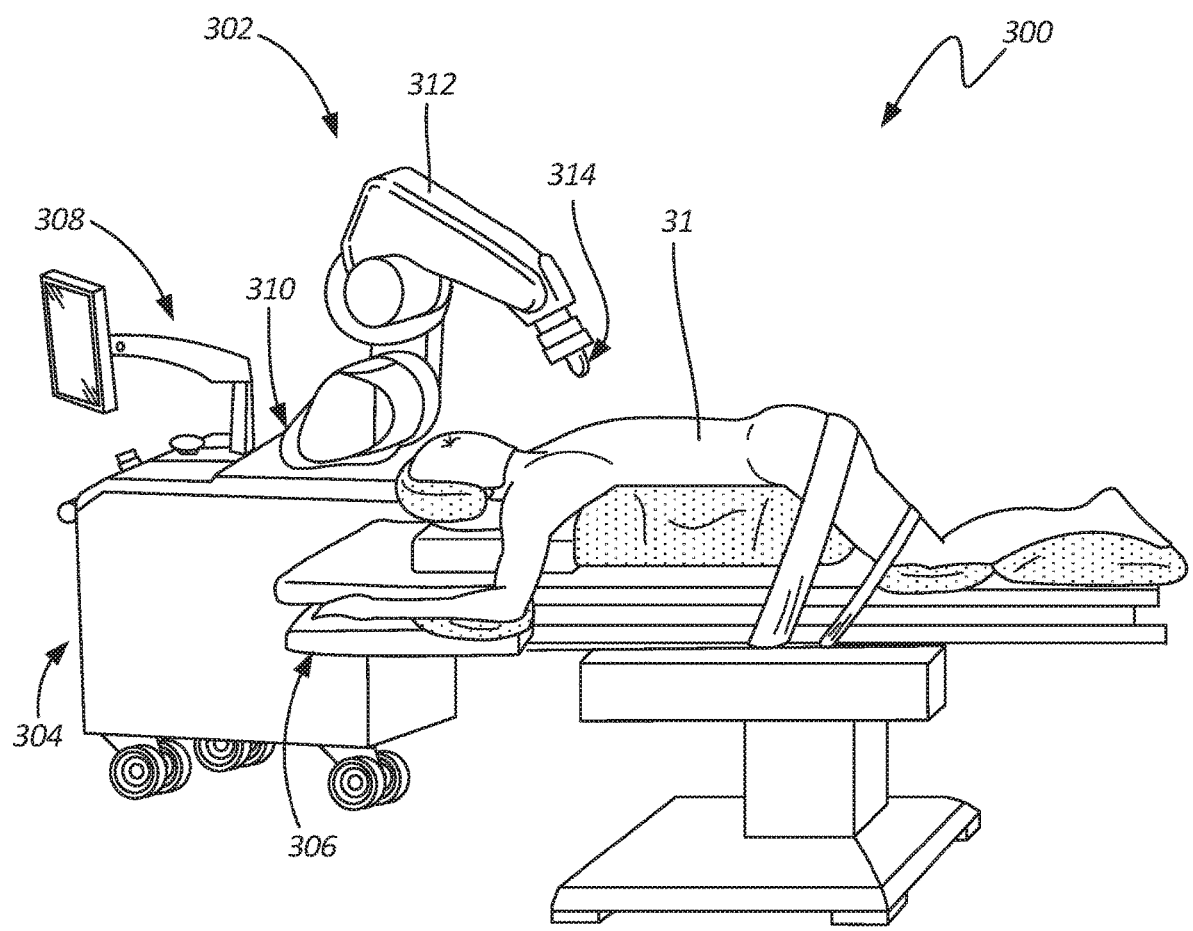
FIG. 10 illustrates a perspective view of a surgical system, in accordance with at least one example of this disclosure.

FIG. 10 illustrates a perspective view of surgical system 300, in accordance with at least one example of this disclosure. System 300 can include robot 302, cart 304, table 306, and user interface 308. Robot 302 can include mount 310, arm 312, and end effector 314. Also shown in FIG. 10 is patient 31 in a modified prone position.

Cart 304 can be a mobile or fixed cart or table configured to support robot 302 and/or user interface 308. In some examples, cart 304 can include a power source and/or control system for robot 302. Table 306 can be a table, such as a surgical or operating table, configured to support and secure patient 31 in one or more positions during an operation. In some examples, cart 304 and table 306 can be adjustable (e.g., height adjustable) either together or individually. In some examples, cart 304 and table 306 can be secured to each other to prevent relative movement of cart 304 to table 306 during a procedure or operation.

Arm 312 can be secured to cart 304 via mount 310. In some examples, mount 310 can be a rigid coupling and in other examples, mount 310 can be a coupling providing one or more degrees of freedom of arm 312 relative to cart 304. In one example, mount 310 can include a motor (e.g., a servo) and a bearing configured to rotate arm 312 relative to cart 304. Arm 312 can include one or more additional joints, each configured to pivot or rotate to provide a total of two, three, four, and the like degrees of freedom of arm 312.

End effector 314 can be a distal portion of arm 312 and can be configured to releasably receive one or more tools, such as driver 160 and/or 260 discussed above and driver 360 discussed below in FIG. 12. In some examples, end effector 314 can be controlled via arm 312 and user interface 308.

Robot 302 and user interface 308 can be in electric or electromagnetic communication with each other. In some examples, user interface 308 can be used to operate robot 302 and can include a control system therefore as discussed in FIG. 11 below. In some examples, user interface can receive data from robot 302 that can be displayed on a screen of user interface 308. User interface 308 can also include input devices, such as a keyboard, mouse, touchscreen, stylus, and the like, for receiving inputs from a user for controlling operations of robot 302. In some examples, user interface 308 can be used to control robot 302 to drive fasteners into a plate or component secured to a patient, or a bone or tissue of a patient.

In operation of one example of surgical system 300, patient 31 can be positioned on table 306 and cart 304 and robot 302 can be positioned in close proximity to patient 31 and table 306. In some examples, a surgical procedure can be performed where an opening is created on patient 31 allowing access to one or more bones of patient 31. In some examples, a fastener or workpiece, such as a screw, can be loaded onto a driver coupled to end effector 314. User interface 308 can be utilized by a user or physician to operate arm 312 of robot 302 to position the fastener at a desired location of the patient. In some examples, user interface 308 can be used to rotate the driver and drive the fastener into a bone or into a plate or other component. Because the driver can include a torque limiting feature, as discussed above, robot 302 can drive the fastener into a plate, for example, at a desired torque and is substantially prevented from over-torqueing the fastener into the plate. Because robot 302 does not have to track or determine the torque applied to the fastener, the driver can help to simplify the design of robot 302. In other examples, robot 302 can be autonomously operated by a control system to, for example, drive and torque a fastener using a driver coupled to end effector 314.

Figure 11:
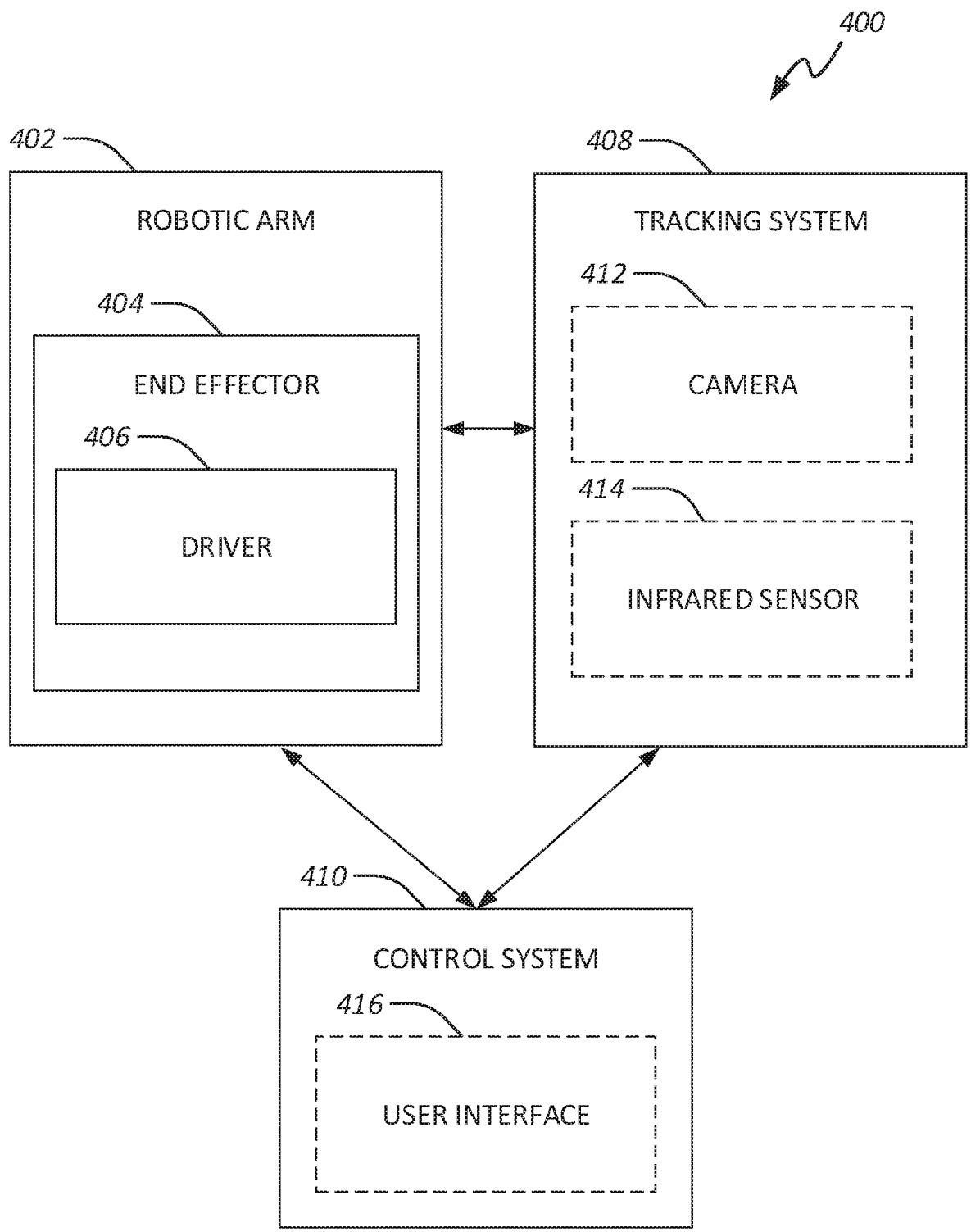
FIG. 11 illustrates a system schematic, in accordance with at least one example of this disclosure.

FIG. 11 illustrates a flow schematic, in accordance with at least one example of this disclosure. System 400 can include robotic arm 402, tracking system 408, and control system 410. Robotic arm 402 can include end effector 404, including driver 406, which can be mounted on end effector 404. Robotic arm 402 can be configured to allow interactive movement and controlled autonomous movement of end effector 404.

Tracking system 408 can optionally include camera 412 or infrared sensor 414. Tracking system 408 can use camera 412 or infrared sensor 414 to track robotic arm 402, end effector 404, driver 406, a target object, and the like. In an example, tracking system 408 can be used to determine a position or an orientation of driver 406. The position or the orientation may be determined relative to a coordinate system or relative to a target object. An example optical tracking device commonly used for this type of application is the Polaris Optical Tracking System from Northern Digital of Waterloo, Ontario, Canada.

Control system 410 can optionally include user interface 416. In another example, user interface 416 can be separate from control system 410 or can be communicatively coupled to control system 410. In some examples, control system 410 can be used to determine a position or orientation of driver 406, such as using the position or the orientation of driver 406, a target object, and/or a coordinate system.

Tracking system 408 may determine a trajectory of driver 406 as it is moved, such as from an interactive force applied to driver 406, end effector 404, or robotic arm 402. Control system 410 may determine that the trajectory would cause robotic arm 402 or a portion of the robotic arm, end effector 404, and driver 406 to a position where a fastener can be driven into a target, such as a plate to be secured to a patient. In one example, once driver 406 has been positioned as desired, control system 410 may establish an interaction zone using anatomical landmarks of the target object (e.g., a target plate) or identified locations of the target object (e.g., digitized locations). The tracking system 408 may determine a position or an orientation of a target object relative to the coordinate system. The position or the orientation of driver 406 may be determined relative to the position or the orientation of the target object by the tracking system. In an example, the coordinate system is determined from the position or the orientation of the target object.

After driver 406 has been positioned relative to the target, driver 406 can be rotated by robotic arm 402 to driver the fastener into the target (e.g., plate). A torque limiter of driver can limit the torque applied by robotic arm 402 to driver 406 and therefore to the fastener to drive the fastener into the plate at a desired torque and to help prevent over-torqueing of the fastener into the target or plate. For example, magnets within a torque limiter of driver 406 can transfer torque, via magnetic coupling, through the torque limiter and to a clutch when the torque is below a threshold torque. When the torque is above a threshold torque, a shaft of the torque limiter can spin relative to a housing of the torque limiter to prevent over-torqueing of the fastener into the plate. By providing a robotic system including a driver that includes a mechanical (magnetic) torque limiter, maintenance and service of the robotic system and torque limiter can be reduced because the magnetic torque limiter can require less-frequent calibration than other torque limiters.

Figure 12:
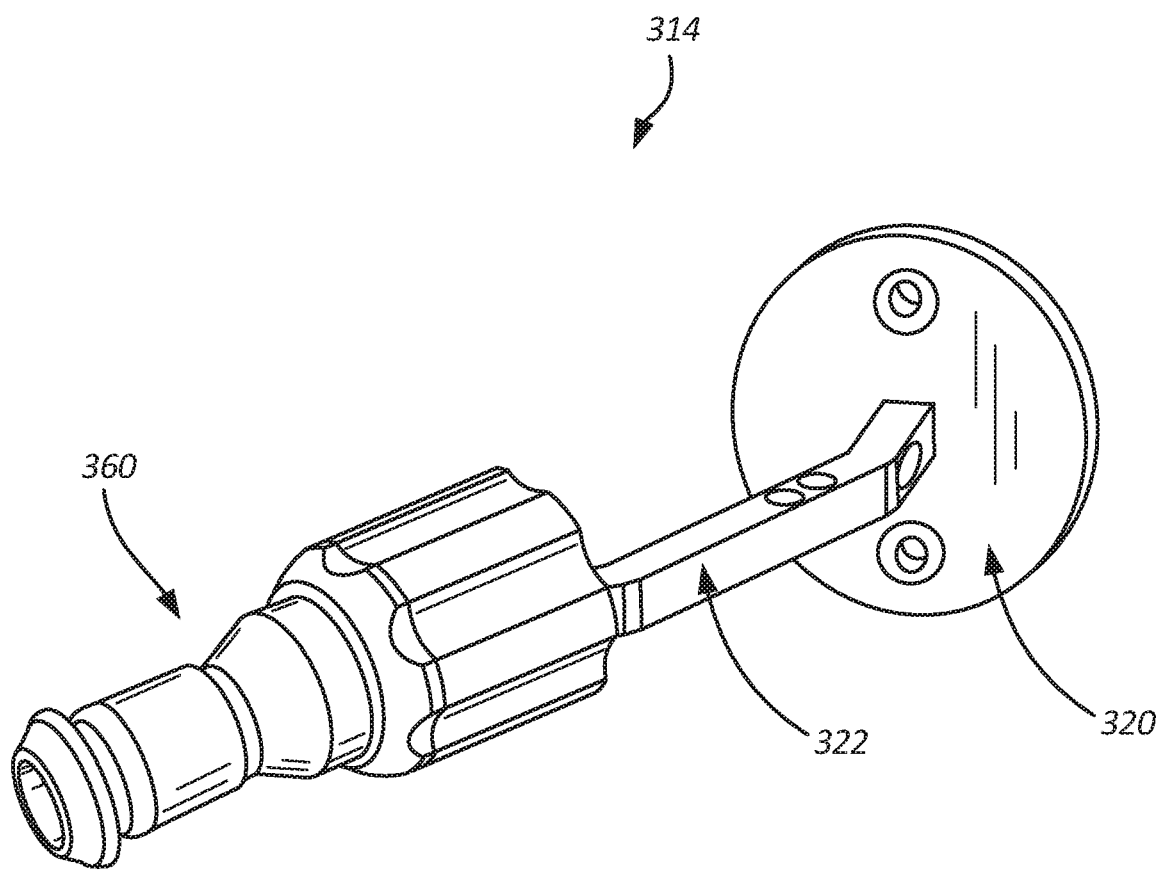
FIG. 12 illustrates a perspective view of a portion of a surgical system, in accordance with at least one example of this disclosure.

FIG. 12 illustrates a perspective view of end effector 314 of FIG. 10, in accordance with at least one example of this disclosure. End effector 314 can include driver 360, flange 320, and arm 322.

Driver 360 can be consistent with drivers 160 and 260 discussed above, except that driver 360 may exclude a handle and may include provisions for releasably coupling to arm 322. For example, a proximal portion of driver 360 can be secured to a distal portion of arm 322 using, for example, screws or bolts.

Flange 320 can be used to secure end effector 314 to arm 312 of robot 302. In some examples, flange 320 can include holes for receiving bolts therethrough for releasably securing flange 320 to arm 312 of robot 302. In some examples, arm 322 can me rotatable independent of flange 320. In other examples, end effector 314 can be rotatable as an assembly. In yet other examples, arm 312 can include a shaft therein (which can be flexible to accommodate the shape of arm 312) to rotation driver 360.

The devices, systems, and methods of this disclosure can offer several benefits over prior art. For example, torque limiter 10 uses magnetic forces to limit torque, rather than mechanical, which can reduce recalibration, because there is little mechanical wear of the torque limiting components. Also, because the methods of this disclosure use permanent magnets to limit torque, the methods can be more reliable than electrical torque limitation methods of the prior art, which can be relatively expensive. The magnetic coupler of this disclosure can require less (re)calibration, and may not have other limitations of an electronic device, such as the need to charge a battery.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A torque limiting driver for driving a workpiece, the torque limiting driver comprising:
   a housing comprising:
      a housing bore comprising a central axis; and
      a housing magnet located proximate the housing bore;
   a shaft located within the housing bore, the shaft comprising:
      a shaft magnet located within the housing bore, the shaft magnet facing the housing and radially alignable with the housing magnet to generate a magnetic coupling to the housing magnet to enable transmission of a torque between the housing and the shaft, wherein the magnetic coupling is configured to uncouple from the housing magnet allowing the shaft and the shaft magnet to rotate about the central axis within the housing when a threshold torque is reached; and
      a clutch connected to the shaft and configured to transfer the torque from the shaft to a workpiece unidirectionally;
   a coupler removably coupleable to a distal end of the clutch, the coupler configured to releasably receive a driver therein;
   a proximal bearing coupled to a proximal portion of the housing and a proximal portion of the shaft to enable rotation of the housing relative to the shaft; and
   a distal bearing coupled to a distal portion of the housing and a distal portion of the shaft to enable rotation of the housing relative to the shaft;
   wherein the shaft defines a shaft bore extending through the shaft along a longitudinal axis of the shaft, the shaft bore defines a first diameter adjacent the proximal bearing, a second diameter adjacent the housing magnet, and a third diameter adjacent the distal bearing, wherein the second diameter is larger than the first diameter and the third diameter.

2. The torque limiting driver of claim 1, further comprising:
   a handle coupleable to the housing to transfer a torque thereto.

3. The torque limiting driver of claim 1, wherein the housing magnet further comprises:
   a plurality of housing magnets disposed around the housing bore.

4. The torque limiting driver of claim 3, wherein the shaft magnet further comprises:
   a plurality of shaft magnets disposed within the shaft and, the shaft magnets coupleable with the plurality of housing magnets.

5. The torque limiter of claim 2, wherein the plurality of shaft magnets are arranged in alternating polarity and the plurality of housing magnets are arranged in alternating polarity to resist uncoupling between the housing magnets and the shaft magnets.

6. The torque limiting driver of claim 1, wherein the clutch includes a ratcheting mechanism.

7. The torque limiting driver of claim 1, the clutch further comprising:
   a driving member connected to a distal portion of the shaft, the driving member rotatable with the shaft when the shaft receives a torque from the housing; and
   a driven member engaging the driving member, the driving member configured to rotate the driven member using the torque when the torque is in a first direction about the central axis and configured to rotate independently of the torque when the torque is in a second direction about the central axis.

8. The torque limiting driver of claim 7, the driven member further comprising a driver releaseably engageable with a workpiece to transfer a torque from the driver to the workpiece.

9. The torque limiting driver of claim 1, wherein the clutch and the housing are not in contact with each other.

10. The torque limiting driver of claim 1, the shaft further comprising:
    the shaft bore extending axially through the shaft.

11. The torque limiting driver of claim 10, wherein the shaft bore comprises a diameter that varies between a proximal end and a distal end of the shaft.

12. The torque limiting driver of claim 1, wherein an outer surface of the housing is axially fluted.

13. The torque limiting driver of claim 1, wherein the housing is configured to substantially shield magnetic fields from extending beyond the torque limiter.

14. A torque limiting driver for driving a workpiece, the torque limiting driver comprising:
   a housing comprising:
      a housing bore comprising a central axis; and
      a housing magnet located proximate the housing bore;
   a shaft located within the housing bore, the shaft comprising:
      a shaft magnet located within the housing bore, the shaft magnet facing the housing and radially alignable with the housing magnet to generate a magnetic coupling to the housing magnet to enable transmission of a torque between the housing and the shaft, wherein the magnetic coupling is configured to uncouple from the housing magnet allowing the shaft and the shaft magnet to rotate about the central axis within the housing when a threshold torque is reached; and
      a clutch connected to the shaft and configured to transfer the torque from the shaft to a workpiece unidirectionally;
   a coupler removably coupleable to a distal end of the clutch, the coupler configured to releasably receive a driver therein;
   a proximal bearing coupled to a proximal portion of the housing and a proximal portion of the shaft to enable rotation of the housing relative to the shaft; and
   a distal bearing coupled to a distal portion of the housing and a distal portion of the shaft to enable rotation of the housing relative to the shaft;
   wherein the proximal bearing includes an inner race connected to the shaft, an outer race connected to the housing, and a plurality of rollers located between the inner race and the outer race of the proximal bearing, and wherein the distal bearing includes an inner race connected to the shaft, an outer race connected to the housing and a plurality of rollers located between the inner race and the outer race of the distal bearing.

15. The torque limiting driver of claim 14, further comprising:
   a handle coupleable to the housing to transfer a torque thereto.

16. The torque limiting driver of claim 14, wherein the housing magnet further comprises:
   a plurality of housing magnets disposed around the housing bore.

17. The torque limiting driver of claim 16, wherein the shaft magnet further comprises:
   a plurality of shaft magnets disposed within the shaft and, the shaft magnets coupleable with the plurality of housing magnets.

18. The torque limiting driver of claim 14, wherein the clutch includes a ratcheting mechanism.

19. The torque limiting driver of claim 14, the clutch further comprising:
   a driving member connected to a distal portion of the shaft, the driving member rotatable with the shaft when the shaft receives a torque from the housing; and
   a driven member engaging the driving member, the driving member configured to rotate the driven member using the torque when the torque is in a first direction about the central axis and configured to rotate independently of the torque when the torque is in a second direction about the central axis.

* * * * *